United States Patent [19]
Crueger et al.

[11] Patent Number: 5,753,501
[45] Date of Patent: May 19, 1998

[54] ACARBOSE BIOSYNTHESIS GENES FROM ACTINOPLANES SP., PROCESS FOR THE ISOLATION THEREOF AND THE USE THEREOF

[75] Inventors: Anneliese Crueger, Erkrath; Wolfgang Piepersberg, Wuppertal; Jürgen Distler, Wuppertal; Ansgar Stratmann, Wuppertal, all of Germany

[73] Assignee: Bayer Aktiengesellschaft, Leverkusen, Germany

[21] Appl. No.: 606,322

[22] Filed: Feb. 23, 1996

[30] Foreign Application Priority Data

Mar. 2, 1995 [DE] Germany .................. 195 07 214.6

[51] Int. Cl.$^6$ .......................... C12N 15/63; C07H 21/04
[52] U.S. Cl. ........................ 435/320.1; 536/23.74
[58] Field of Search ................. 536/23.74; 435/320.1; 935/77, 78

[56] References Cited

U.S. PATENT DOCUMENTS

| | | | |
|---|---|---|---|
| 3,876,766 | 4/1975 | Frommer et al. | 424/115 |
| 4,019,960 | 4/1977 | Frommer et al. | 195/80 R |
| 4,062,950 | 12/1977 | Frommer et al. | 424/181 |

OTHER PUBLICATIONS

Piepersberg W., Critical Rev. Biotechnol. (1994)14(3), 251–285.
Sanger, F. et al., (1977), Proc. Natl. Acad. Sci. USA, 74, 5463–5467.
Southern E.M., (1975), J. Mol. Biol., 98, 503–517.
Stockmann, M. and Piepersberg W., FEMS Microbiology Letter, 90, 185–190.
Linton et al. Gene (1995) 153: 33–40.
Pissowotzki et al. Mol. Gen. Genet. (1991) 231:113–123.
Merson–Davies et al. Molecular Microbiol. (1994) 13(2):349–355.
Martin, J.F., J. Ind. Microbiol. 9, 73–90 (1992).
Chater, K.F., Ciba Found. Symp., 171:144–62(1992).
J. Sambrook et al., Molecular Cloning, A Lab. Manual, 2nd Edition, 1989, Cold Spring Harbour Lab. Press, N.Y., USA.
Birnboim H.D. & Doly J. (1979), Nucleic Acids Res., 7, 1513–1523.
Hanahan D. (1983), J. Mol. Biol., 166, 557–580.
Hopwood D.A. et al., (1985), A laboratory manual, The John Innes Foundation, Norwich, England "Genetic manipulation of Streptomyces", p. 1.

*Primary Examiner*—Lisa B. Arthur
*Attorney, Agent, or Firm*—Sprung Kramer Schaefer & Briscoe

[57] ABSTRACT

The invention relates to acarbose biosynthesis genes from actinomycetes, predominantly from Actinoplanes sp. SE 50/110 and its mutants, to a process for the isolation of acarbose biosynthesis genes from actinomycetes using a gene probe which has been derived from highly conserved protein regions of known dTDP-glucose dehydratase enzymes for finding the genes acbA (coding for dTDP-glucose synthase), acbB (coding for dTDP-glucose dehydratase) and acbC (coding for a cyclase, in part identical to AroB, bacterial 3-dehydroquinate synthases) or one or more acarbose biosynthesis genes from Actinoplanes sp., and to the use of the acarbose biosynthesis genes.

2 Claims, 10 Drawing Sheets

Sequencing strategy for the BamHI fragment cloned in plasmid pAS2.

Fig. 1 Sequencing strategy for the BamHI fragment cloned in plasmid pAS2.

Fig. 14A acbC ---> (N-terminal part lacking)

```
1/1                                              31/11
    ile arg glu tyr phe thr his his gly ile asp his ser ile leu val met arg val gly
    GGA TCC GGG AGT ACT TCA CCC ATC ACG GCA TCG ATC ATT CGA TCC TGG TGA TGC GGG TGG
    CCT AGG CCC TCA TGA AGT GGG TAG TGC CGT AGC TAG TAA GCT AGG ACC ACT ACG CCC ACC 61/21                                            91/31
    glu thr val lys asp phe asp thr ala gly arg ile val ala ala met asp ala phe gly
    GCG AGA CGG TCA AGG ACT TCG ACA CGG CGG GCC GCA TCG TCG CCG CGA TGG ACG CCT TCG
    CGC TCT GCC AGT TCC TGA AGC TGT GCC GCC GGC CGT AGC AGC GGC GCT ACC TGC GGA AGC 121/41                                           151/51
    leu ala arg arg arg glu pro met ile val val gly gly gly val leu met asp val ala
    GAC TGG CCC GCC GCC GGG AGC CGA TGA TCG TCG TCG GTG GTG GGG TGC TGA TGG ACG TGG
    CTG ACC GGG CGG CGG CCC TCG GCT ACT AGC AGC AGC CAC CAC CCC ACG ACT ACC TGC ACC 181/61                                           211/71
    gly leu val ala ser leu tyr arg ala arg his ala val leu arg val pro thr thr leu
    CCG GTC TGG TGG CCA GCC TCT ACc GGG CGC GGC ACG CCG TTC TGC GGG TGC CGA CGA CAC
    GGC CAG ACC ACC GGT CGG AGA TGg CCC GCG CCG TGC GGC AAG ACG CCC ACG GCT GCT GTG 241/81                                           271/91
    val gly leu ile asp ala val ser arg glu asp arg val asn phe asn gly his lys glu
    TGG TCG GAC TGA TCG ACG CGG TGT CGC GCG AAG ACC GGG TCA ACT TCA ACG GCC ACA AGG
    ACC AGC CTG ACT AGC TGC GCC ACA GCG CGC TTC TGG CCC AGT TGA AGT TGC CGG TGT TCC 301/101                                          331/111
    pro ala gly tyr val arg pro ala asp leu thr leu leu asp arg arg phe leu ala thr
    AAC CGG CTG GGT ACG TAC GCC CGG CTG ATC TGA CCC TGC TGG ACC GCC GCT TCC TGG CCA
    TTG GCC GAC CCA TGC ATG CGG GCC GAC TAG ACT GGG ACG ACC TGG CGG CGA AGG ACC GGT 361/121                                          391/131
    leu asp arg arg his leu ser asn gly leu ala glu met leu lys ile ala leu ile lys
    CCC TGG ACC GGC GCC ACC TCA GCA ACG GGC TCG CCG AGA TGC TCA AGA TCG CGC TGA TCA
    GGG ACC TGG CCG CGG TGG AGT CGT TGC CCG AGC GGC TCT ACG AGT TCT AGC GCG ACT AGT 421/141                                          451/151
    asp ala glu leu phe gln leu leu glu arg his gly arg val leu ile glu glu arg phe
    AGG ATG CCG AGC TGT TCC AGC TGC TGG AGC GGC ACG GGC GGG TCC TGA TCG AGG AAC GGT
    TCC TAC GGC TCG ACA AGG TCG ACG ACC TCG CCG TGC CCG CCC AGG ACT AGC TCC TTG CCA 481/161                                          511/171
    gln gly val pro glu pro val thr gly pro pro ser gly pro cys ala arg his pro trp
    TCC AGG GCG TAC CGG AAC CGG TGA CCg GGC CGC CGT CCG GGc CCT GCG CGC GCC ACC CAT
    AGG TCC CGC ATG GCC TTG GCC ACT GGc CCG GCG GCA GGC CCg GGA CGC GCG CGG TGG GTA 541/181                                          571/191
    his ala gly gly thr arg pro asn leu trp glu ser arg leu glu arg ser val asp tyr
    GGC ATG CTG GAG GAA CTC GGC CCa ATC TGT GGG AGA GCC GGC TGG AAC GCA GTG TCG ACT
    CCG TAC GAC CTC CTT GAG CCG GGt TAG ACA CCC TCT CGG CCG ACC TTG CGT CAC AGC TGA 601/201                                          631/211
    gly his thr phe ser pro thr ile glu met arg ala leu pro ala leu leu his gly glu
    ACG GGC ACA CGT TCA GCC CGA CCA TCG AGA TGC GCG CGC TGC CGG CTC TGC TGC ACG GCG
    TGC CCG TGT GCA AGT CGG GCT GGT AGC TCT ACG CGC GCG ACG GCC GAG ACG ACG TGC CGC 661/221                                          691/231
    ala val cys val asp met ala leu thr thr val leu ala tyr arg arg gly leu leu asp
    AGG CCG TGT GTG TGG ACA TGG CGC TGA CCA CGG TGC TGG CGT ACC GGC GGG GTC TGC TCG
    TCC GGC ACA CAC ACC TGT ACC GCG ACT GGT GCC ACG ACC GCA TGG CCG CCC CAG ACG AGC 721/241                                          751/251
    val ala gln arg asp arg ile phe ala val met thr ala leu gly leu pro thr gly ile
    ACG TCG CGC AGC GGG ACC GGA TCT TCG CGG TGA TCA CCG CCC TGG GCC TGC CGA CCG GCA
    TGC AGC GCG TCG CCC TGG CCT AGA AGC GCC ACT ACT GGC GGG ACC CGG ACG GCT GGC CGT
```

Fig. 14B

```
781/261                                   811/271
     arg leu leu thr pro glu val leu glu ala ala leu gln asp thr val arg his arg asp
     TCC GCC TGC TCA CGC CGG AGG TGC TGG AGG CGG CGT TGC AGG ACA CCG TCC GGC ACC GGG
     AGG CGG ACG AGT GCG GCC TCC ACG ACC TCC GCC GCA ACG TCC TGT GGC AGG CCG TGG CCC 841/281                                   871/291
     gly trp gln arg leu pro leu pro val gly ile gly gly val thr phe val asn asp val
     ACG GGT GGC AGC GGC TGC CAC TGC CGG TGG GGA TCG GGG GTG TCA CGT TCG TCA ACG ACG
     TGC CCA CCG TCG CCG ACG GTG ACG GCC ACC CCT AGC CCC CAC AGT GCA AGC AGT TGC TGC 901/301                                   931/311
     thr ala ala glu leu gln pro pro arg OPA
     TGA CGG CCG CCG AGC TGC AGC CGC CGC GCT GAT GCA GCA CCG GCT CGC CGA GGA CGC CCT
     ACT GCC GGC GGC TCG ACG TCG GCG GCG CGA CTA CGT CGT GGC CGA GCG GCT CCT GCG GGA 961/321                                   991/331
     GCT GCT GCG CGC CCT AGC TCG GGC CGC GGA CGC CGA TCG CCG GAA GCG ACC GGC GTC cGT
     CGA CGA CGC GCG GGA TCG AGC CCG GCG CCT GCG GCT AGC GGC CTT CGC TGG CCG CAG gCA
                                    AMB ser pro gly arg val gly ile ala pro leu ser arg arg gly asp 1021/341                                  1051/351
     CCG CCC ACC GGT TGC CGT CAG TCC ACC AGG AAC GGT TGG CGC GAT ACC ACG CGA CCG TTT
     GGC GGG TGG CCA ACG GCA GTC AGG TGG TCC TTG CCA ACC GCG CTA TGG TGC GCT GGC AAA
     ala trp arg asn gly asp thr trp trp ser arg asn ala arg tyr trp ala val thr glu 1081/361                                  1111/371
     CCG CGA TGC CGT CGG TGA AAT CGA CCC GCG GCC GGT AAC CGA GTT CCC CGG CGA TTT TCG
     GGC GCT ACG GCA GCC ACT TTA GCT GGG CGC CGG CCA TTG GCT CAA GGG GCC GCT AAA AGC
     ala ile gly asp thr phe asp val arg pro arg tyr gly leu glu gly ala ile lys ser 1141/381                                  1171/391
     AAT AGT CGA GAG AAT AGC GCC GGT CGT GAC CTT TGC GAT CGG TCA CGA AAG ATA TGC GCG
     TTA TCA GCT CTC TTA TCG CGG CCA GCA CTG GAA ACG CTA GCC AGT GCT TTC TAT ACG CGC
     tyr asp leu ser tyr arg arg asp his gly lys arg asp thr val phe ser ile arg ser 1201/401                                  1231/411
     AAC GCC GGG CGC CGC ACG CCT CGA GGA GGA TCT CGG TCA ATT CGA GAT TCG TCG CCT CCC
     TTG CGG CCC GCG GCG TGC GGA GCT CCT CCT AGA GCC AGT TAA GCT CTA AGC AGC GGA GGG
     arg arg ala gly cys ala glu leu leu ile glu thr leu glu leu asn thr ala glu trp 1261/421                                  1291/431
     ACC CAC CGC CGA TGT GAT AGA CCT CGC CTG CCC GGC CGG CAC CCA GGG CCA GGG CgA GAC
     TGG GTG GCG GCT ACA CTA TCT GGA GCG GAC GGG CCG GCC GTG GGT CCC GGT CCC GcT CTG
     gly gly gly ile his tyr val glu gly ala arg gly ala gly leu ala leu ala leu gly 1321/441                                  1351/451
     cGC GGC AAT GGT CGC TGA CGT GGA GCC AGT CGC GGA TGT TGC GGC CGT CGC CGT AgA CCg
     gCG CCG TTA CCA GCG ACT GCA CCT CGG TCA GCG CCT ACA ACG CCG GCA GCG GCA TcT GGc
     arg cys his asp ser val his leu trp asp arg ile asn arg gly asp gly tyr val pro 1381/461                                  1411/471
     GtA CGT CGA GCc cgT CGA GCA GCC TGG TGA CGA ACA gcG GAA TCA TTT TCT CCG GGA ATT
     CaT GCA GCT CCg gcA GCT CGT CGG ACC ACT GCT TGT cgC CTT AGT AAA AGA GGC CCT TAA
     val asp leu gly asp leu leu arg thr val phe leu pro ile met lys glu pro phe gln 1441/481                                  1471/491
     GCC GGG GCC CGT AGT TGT TGG AGC AGC GGG TCA CCA CGA CGT CCA TCC CGT GCG TCT GGT
     CGG CCC CGG GCA TCA ACA ACC TCG TCG CCC AGT GGT GCT GCA GGT AGG GCA CGC AGA CCA
     arg pro gly tyr asn asn ser cys arg thr val val val asp met gly his thr gln his 1501/501                                  1531/511
     GGT AGG CCA GAG CGA GGA GGT CGG ACC CGG CTT TGC TCG CGG CGT ACG GCG AGT TGG GCG
     CCA TCC GGT CTC GCT CCT CCA GCC TGG GCC GAA ACG AGC GCC GCA TGC CGC TCA ACC CGC
     tyr ala leu ala leu leu asp gly ala lys ser ala ala tyr pro ser asn pro ala
```

Fig. 14C

```
1561/521                              1591/531
CCA GCG GAT GGC CCT CGG CCC ACG AGC CGG TGT CGA TCG ACC CGT ACA CCT CGT CGG TGG
GGT CGC CTA CCG GGA GCC GGG TGC TCG GCC ACA GCT AGC TGG GCA TGT GGA GCA GCC ACC
 leu pro his gly glu ala trp ser gly thr asp ile ser gly tyr val glu asp thr ser 1621/541                              1651/551
AAA CAT GCA GGA AGC GGC CGA TAT GGT GGC GTA GCG CGG CGT CCA GTA GCA CCT GAG TGC
TTT GTA CGT CCT TCG CCG GCT ATA CCA CCG CAT CGC GCC GCA GGT CAT CGT GGA CTC ACG
 val his leu phe arg gly ile his his arg leu ala ala asp leu leu val gln thr gly 1681/561                              1711/571
CGA CCA GGT TGC TGG CCA CGA AGG GGC CGG AGG CGA CCA CCG AGC GGT CGA CGT GGG TCT
GCT GGT CCA ACG ACC GGT GCT TCC CCG GCC TCC GCT GGT GGC TCG CCA GCT GCA CCC AGA
 val leu asn ser ala val phe pro gly ser ala val val ser arg asp val his thr glu 1741/581                              1771/591
CGG CGG CGA AGT GCG CCA CGG TGT CGT GCC GCG CCA TCA GCC CCT CGA TTA GAC CTT CGT
GCC GCC GCT TCA CGC GGT GCC ACA GCA CGG CGC GGT AGT CGG GGA GCT AAT CTG GAA GCA
 ala ala phe his ala val thr asp his arg ala met leu gly glu ile leu gly glu asp 1801/601                              1831/611
CAC AGA TGT CGC CCC GAA CGA AGC TGA AAC GAG GGT CCG CCG ACG CTT CGG CGA GAT TTC
GTG TCT ACA GCG GGG CTT GCT TCG ACT TTG CTC CCA GGC GGC TGC GAA GCC GCT CTA AAG
 cys ile asp gly arg val phe ser phe arg pro asp ala ser ala glu ala leu asn arg 1861/621                              1891/631
TGA GAT TGC CTC CGT AAC CCA GTT TGT CGA CGA CCG TAA CCT GCG TCA CGG GTT GTG GTG
ACT CTA ACG GAG GCA TTG GGT CAA ACA GCT GCT GGC ATT GGA CGC AGT GCC CAA CAC CAC
 leu asn gly gly tyr gly leu lys asp val val thr val gln thr val pro gln pro thr 1921/641                              1951/651
TGG CAA TGT CGC CAC TGA TCA GGG AAG TTA CAA AAT GGG ACC CGA TAA AGC CGG CTC CGC
ACC GTT ACA GCG GTG ACT AGT CCC TTC AAT GTT TTA CCC TGG GCT ATT TCG GCC GAG GCG
 ala ile asp gly ser ile leu ser thr val phe his ser gly ile phe gly ala gly gly 1981/661                              2011/671
CGG TGA CCA AGA TTT TCA TCG CCG GGA TTG TAG CAA TGC CGC CAA TGG GTG CCC GAT GTT
GCC ACT GGT TCT AAA AGT AGC GGC CCT AAC ATC GTT ACG GCG GTT ACC CAC GGG CTA CAA
 thr val leu ile lys met    <--- acbB 2041/681                              2071/691
                                      acbA --->  met arg gly ile leu leu ala
CGG CCG AGC CAT TTA CGG GGC TTG CTG ATA TGG TCG GTC ACG TGC GCG AAA TAT TGC TGG
GCC GGC TCG GTA AAT GCC CCG AAC GAC TAT ACC AGC CAG TGC ACG CGC TTA TAC GAC C 2101/701                              2131/711
 gly gly thr gly ser arg leu arg pro val thr trp ala val ser lys gln leu met pro
CCG GGG GAA CCG GCT CAC GGC TTC GAC CGG TGA CCT GGG CGG TTT CCA AAC AAC TGA TGC
GGC CCC CTT GGC CGA GTG CCG AAG CTG GCC ACT GGA CCC GCC AAA GGT TTG TTG ACT ACG 2161/721                              2191/731
 val tyr asp lys pro met ile tyr tyr pro leu ala thr leu val ser cys gly
CGG TCT ATG ACA AAC CGA TGA TCT ACT ATC CGC TGG CCA CGC TCG TCA GCT GCG GA
GCC AGA TAC TGT TTG GCT ACT AGA TGA TAG GCG ACC GGT GCG AGC AGT CGA CGC CT 2221/741
 ser
TCC
AGG
```

DNA sequence of the 2.2kb BamHI fragment, and the amino-acid sequence of the genes acb A, B, C.

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 2219 Nucleotides
        ( B ) TYPE: Nucleic Acid
        ( C ) STRANDEDNESS: Double
        ( D ) TOPOLOGY: Linear     ( i i ) MOLECULE TYPE: Genomic DNA     ( i i i ) HYPOTHETICAL: No     ( i v ) ANTI-SENSE: No     ( v i ) ORIGINAL SOURCE:
        ( A ) ORGANISM: Actinoplanes sp. SE 50/110

( x i ) SEQUENCE DESCRIPTION: SEQ ID NO:1:

```
GGATCCGGGA  GTACTTCACC  CATCACGGCA  TCGATCATTC                    40
GATCCTGGTG  ATGCGGGTGG  GCGAGACGGT  CAAGGACTTC                    80
GACACGGCGG  GCCGCATCGT  CGCCGCGATG  GACGCCTTCG                   120
GACTGGCCCG  CCGCCGGGAG  CCGATGATCG  TCGTCGGTGG                   160
TGGGGTGCTG  ATGGACGTGG  CCGGTCTGGT  GGCCAGCCTC                   200
TACCGGGCGC  GGCACGCCGT  TCTGCGGGTG  CCGACGACAC                   240
TGGTCGGACT  GATCGACGCG  GTGTCGCGCG  AAGACCGGGT                   280
CAACTTCAAC  GGCCACAAGG  AACCGGCTGG  GTACGTACGC                   320
CCGGCTGATC  TGACCCTGCT  GGACCGCCGC  TTCCTGGCCA                   360
CCCTGGACCG  GCGCCACCTC  AGCAACGGGC  TCGCCGAGAT                   400
GCTCAAGATC  GCGCTGATCA  AGGATGCCGA  GCTGTTCCAG                   440
CTGCTGGAGC  GGCACGGGCG  GGTCCTGATC  GAGGAACGGT                   480
TCCAGGGCGT  ACCGGAACCG  GTGACCGGGC  CGCCGTCCGG                   520
GCCCTGCGCG  CGCCACCCAT  GGCATGCTGG  AGGAACTCGG                   560
CCCAATCTGT  GGGAGAGCCG  GCTGGAACGC  AGTGTCGACT                   600
ACGGGCACAC  GTTCAGCCCG  ACCATCGAGA  TGCGCGCGCT                   640
GCCGGCTCTG  CTGCACGGCG  AGGCCGTGTG  TGTGGACATG                   680
GCGCTGACCA  CGGTGCTGGC  GTACCGGCGG  GGTCTGCTCG                   720
ACGTCGCGCA  GCGGGACCGG  ATCTTCGCGG  TGATGACCGC                   760
CCTGGGCCTG  CCGACCGGCA  TCCGCCTGCT  CACGCCGGAG                   800
GTGCTGGAGG  CGGCGTTGCA  GGACACCGTC  CGGCACCGGG                   840
ACGGGTGGCA  GCGGCTGCCA  CTGCCGGTGG  GGATCGGGGG                   880
TGTCACGTTC  GTCAACGACG  TGACGGCCGC  CGAGCTGCAG                   920
CCGCCGCGCT  GATGCAGCAC  CGGCTCGCCG  AGGACGCCCT                   960
```

-continued

| | | | | |
|---|---|---|---|---|
| GCTGCTGCGC | GCCCTAGCTC | GGGCCGCGGA | CGCCGATCGC | 1000 |
| CGGAAGCGAC | CGGCGTCCGT | CCGCCCACCG | GTTGCCGTCA | 1040 |
| GTCCACCAGG | AACGGTTGGC | GCGATACCAC | GCGACCGTTT | 1080 |
| CCGCGATGCC | GTCGGTGAAA | TCGACCCGCG | GCCGGTAACC | 1120 |
| GAGTTCCCCG | GCGATTTTCG | AATAGTCGAG | AGAATAGCGC | 1160 |
| CGGTCGTGAC | CTTTGCGATC | GGTCACGAAA | GATATGCGCG | 1200 |
| AACGCCGGGC | GCCGCACGCC | TCGAGGAGGA | TCTCGGTCAA | 1240 |
| TTCGAGATTC | GTCGCCTCCC | ACCCACCGCC | GATGTGATAG | 1280 |
| ACCTCGCCTG | CCCGGCCGGC | ACCCAGGGCC | AGGGCGAGAC | 1320 |
| CGCGGCAATG | GTCGCTGACG | TGGAGCCAGT | CGCGGATGTT | 1360 |
| GCGGCCGTCG | CCGTAGACCG | GTACGTCGAG | CCCGTCGAGC | 1400 |
| AGCCTGGTGA | CGAACAGCGG | AATCATTTTC | TCCGGGAATT | 1440 |
| GCCGGGGCCC | GTAGTTGTTG | GAGCAGCGGG | TCACCACGAC | 1480 |
| GTCCATCCCG | TGCGTCTGGT | GGTAGGCCAG | AGCGAGGAGG | 1520 |
| TCGGACCCGG | CTTTGCTCGC | GGCGTACGGC | GAGTTGGGCG | 1560 |
| CCAGCGGATG | GCCCTCGGCC | CACGAGCCGG | TGTCGATCGA | 1600 |
| CCCGTACACC | TCGTCGGTGG | AAACATGCAG | GAAGCGGCCG | 1640 |
| ATATGGTGGC | GTAGCGCGGC | GTCCAGTAGC | ACCTGAGTGC | 1680 |
| CGACCAGGTT | GCTGGCCACG | AAGGGGCCGG | AGGCGACCAC | 1720 |
| CGAGCGGTCG | ACGTGGGTCT | CGGCGGCGAA | GTGCGCCACG | 1760 |
| GTGTCGTGCC | GCGCCATCAG | CCCCTCGATT | AGACCTTCGT | 1800 |
| CACAGATGTC | GCCCCGAACG | AAGCTGAAAC | GAGGGTCCGC | 1840 |
| CGACGCTTCG | GCGAGATTTC | TGAGATTGCC | TCCGTAACCC | 1880 |
| AGTTTGTCGA | CGACCGTAAC | CTGCGTCACG | GGTTGTGGTG | 1920 |
| TGGCAATGTC | GCCACTGATC | AGGGAAGTTA | CAAAATGGGA | 1960 |
| CCCGATAAAG | CCGGCTCCGC | CGGTGACCAA | GATTTCATC | 2000 |
| GCCGGGATTG | TAGCAATGCC | GCCAATGGGT | GCCCGATGTT | 2040 |
| CGGCCGAGCC | ATTTACGGGG | CTTGCTGATA | TGGTCGGTCA | 2080 |
| CTGGCGCGGA | ATATTGCTGG | CCGGGGGAAC | CGGCTCACGG | 2120 |
| CTTCGACCGG | TGACCTGGGC | GGTTTCCAAA | CAACTGATGC | 2160 |
| CGGTCTATGA | CAAACCGATG | ATCTACTATC | CGCTGGCCAC | 2200 |
| GCTCGTCAGC | TGCGGATCC | | | 2219 |

( 2 ) INFORMATION FOR SEQ ID NO: 2:

( i ) SEQUENCE CHARACTERISTICS:
        ( A ) LENGTH: 21 Nucleotides
        ( B ) TYPE: Nucleic Acid
        ( C ) STRANDEDNESS: Single
        ( D ) TOPOLOGY: Linear     ( x i ) SEQUENCE DESCRIPTION: SEQ ID NO:2:

GCCGCCGAAT CCCATGTGGA C        21

( 2 ) INFORMATION FOR SEQ ID NO: 3:

(i) SEQUENCE CHARACTERISTICS:
    (A) LENGTH: 24 Nucleotides
    (B) TYPE: Nucleic Acid
    (C) STRANDEDNESS: Single
    (D) TOPOLOGY: Linear (xi) SEQUENCE DESCRIPTION: SEQ ID NO:3:

CCCGTAGTTG TTGGAGCAGC GGGT                                              24

(2) INFORMATION FOR SEQ ID NO: 4:

(i) SEQUENCE CHARACTERISTICS:
    (A) LENGTH: 17 Nucleotides
    (B) TYPE: Nucleic Acid
    (C) STRANDEDNESS: Single
    (D) TOPOLOGY: Linear (xi) SEQUENCE DESCRIPTION: SEQ ID NO:4:

GTAAAACGAC GGCCAGT                                                      17

(2) INFORMATION FOR SEQ ID NO: 5:

(i) SEQUENCE CHARACTERISTICS:
    (A) LENGTH: 18 Nucleotides
    (B) TYPE: Nucleic Acid
    (C) STRANDEDNESS: Single
    (D) TOPOLOGY: Linear (xi) SEQUENCE DESCRIPTION: SEQ ID NO:5:

GAAACAGCTA TGACCATG                                                     18

ACARBOSE BIOSYNTHESIS GENES FROM ACTINOPLANES SP., PROCESS FOR THE ISOLATION THEREOF AND THE USE THEREOF

BACKGROUND OF THE INVENTION

1. Field of the Invention

The invention relates to acarbose biosynthesis genes from actinomycetes, predominantly from Actinoplanes sp. SE 50/110 and its mutants, to a process for the isolation of acarbose biosynthesis genes from actinomyces using a gene probe which has been derived from highly conserved protein regions of known dTDP-glucose dehydratase enzymes for finding the genes acbA (coding for dTDP-glucose synthase), acbB (coding for dTDP-glucose dehydratase) and acbC (coding for a cyclase, in part identical to AroB, bacterial 3-dehydroquinate synthases) or one or more acarbose biosynthesis genes from Actinoplanes sp., and to the use of the acarbose biosynthesis genes.

2. Description of the Related Art Including Information Disclosed Under 37 CFR 1.97-1.99

Earlier patent applications (for example DE 2 064 092, DE 2 209 834) relate to the finding that a number of actinomycetes, especially the actinoplanaceae, produce oligosaccharide-like inhibitors of glycoside hydrolases, preferably carbohydrate-cleaving enzymes of the digestive tract. The most potent inhibitor of this group described is the compound acarbose, O-4,6-dideoxy-4-[[1S-(1S, 4R, 5S, 6S)-4,5,6-trihydroxy-3-(hydroxymethyl)-2-cyclohexen-1-yl]-amino]-α-D-glucopyranosyl-(1→4)-O-α-D-glucopyranosyl-(1→4)-D-glucopyranose (DE 2 347 782).

Acarbose is used in human medicine for controlling diabetes mellitus. The secondary metabolite acarbose is produced by Actinoplanes sp. SE 50 (CBS No. 961.70) and by a natural variant of this strain, SE 50/110 (CBS 614.71) [DE 22 09 834], and by selectants and mutants thereof. The original isolate came from near Ruiru in Kenya. The isolation of a saccharase inhibitor of this type is described in the said patent applications, for example in Examples 1 to 4 of the said German Patent Application.

It was to be expected from the structure of acarbose that the deoxyglucose part of the acarbose molecule is produced in accordance with the biosynthesis of 6-deoxysaccharide residues of various antibiotics (for example aminoglycosides such as streptomycin, kasugamycin; macrolides such as erythromycin, tylosin; polyenes such as amphotericin A, B, nystatin; anthracyclines such as daunorubicin; glycopeptides such as vancomycin).

It is possible by means of genetic engineering to isolate certain genes directly from the genome, using, for example, gene probes which bind specifically to the required DNA sequence. It is possible in this way to "fish" the gene which is to be isolated out of a large number of unknown sequences.

It is furthermore known in the case of actinomycetes—especially streptomyces—that in the secondary metabolite producers investigated to date the biosynthesis genes are arranged side by side in a cluster on the chromosome, less often on a plasmid [Martin, J. F., J. Ind. Microbiol 9, 73–90 (1992), Chater, K. F., Ciba Found. Symp., 171 (Secondary Metabolites: Their Function and Evolution) 144–62 (1992)]. It is thus possible to isolate, by "fishing" with gene probes, adjacent, hitherto unknown biosynthesis genes whose significance for the required biosynthesis can then be elucidated.

A corresponding application of molecular biological techniques has not hitherto succeeded for actinoplanaceae, nor was it to be expected for this genetically uncharacterized group of organisms.

SUMMARY OF THE INVENTION

Surprisingly, it has now been found that a gene probe which has been derived from highly conserved protein regions of known dTDP-glucose dehydratase enzymes is suitable in Actinoplanes sp. for finding the genes acbA (coding for dTDP-glucose synthase) and acbB (coding for dTDP-glucose dehydratase). It is furthermore surprising that another gene has been found in the form of acbC, which is adjacent to the acbB gene and codes for a cyclase (in part identical to AroB, bacterial 3-dehydroquinate synthases) and is thus involved in the biosynthesis of the unsaturated cyclitol (valienamines).

The present invention relates to:

The complete DNA sequence of acbB and the partial DNA sequences of acbA and acbC.

The complete amino-acid sequence of acbB and the partial amino-acid sequences of acbA and acbC.

A process for isolating secondary metabolite biosynthesis genes from actinomycetes, especially from Actinoplanes, characterized in that a gene probe which has been derived from highly conserved protein regions of known dTDP-glucose dehydratase enzymes is used for finding the genes acbA (coding for dTDP-glucose synthase), acbB (coding for dTDP-glucose dehydratase) and acbC (coding for a cyclase, in part identical to AroB, bacterial 3-dehydroquinate synthases) or one or more acarbose biosynthesis genes from Actinoplanes sp.

A process for isolating biosynthesis genes of acarbose-related natural substances in actinomycetes (for example for validamycin, oligostatins (trestatin), adiposins).

Increasing the acarbose synthetic output in Actinoplanes by an increased gene dose or more effective promoters or by alteration of regulation by genetic manipulation (for example of regulator protein expression or of regulator recognition sites).

Increasing acarbose synthetic output in Actinoplanes by protein engineering in the biosynthesis steps which limit acarbose synthesis (bottleneck enzymes) or to prevent production of additional components. Limitation of the product spectrum in Actinoplanes to the required main product by eliminating unwanted biosynthetic pathways to additional components or unwanted enzymatic breakdown reactions.

Alteration of regulation and thus of the nutrient requirements with a view to improved acarbose productivity in Actinoplanes.

Expression in heterologous host strains (for example in *Streptomyces lividans* and in other streptomycetes, in rapidly growing bacteria such as *E. coli, Bacillus subtilis* or *Corynebacterium glutamicum*, or in yeasts), in order to achieve an increase in production by improved space-time yields, to develop a simplified process for purification, to achieve a specific restriction of the product spectrum.

The use of the acarbose biosynthesis genes for the in vitro synthesis of acarbose or compounds of this class of substances, starting from synthetically or microbially produced precursors.

BRIEF DESCRIPTION OF THE DRAWINGS

The invention will now be further described with reference to the drawings, wherein:

FIGS. 14A, 14B and 14C collectively depict the nucleotide and amino acid sequences of the 2.2 kb BamHI fragment containing the genes acb A,B, C.

DESCRIPTION OF PREFERRED EMBODIMENT(S)

The invention is described in detail hereinafter.

All the genetic engineering methods were, unless otherwise indicated, carried out as in J. Sambrook et al. (Molecular Cloning; A laboratory manual; 2nd edition, 1989; Cold Spring Harbor Laboratory Press, N.Y., USA).

Figure 2:
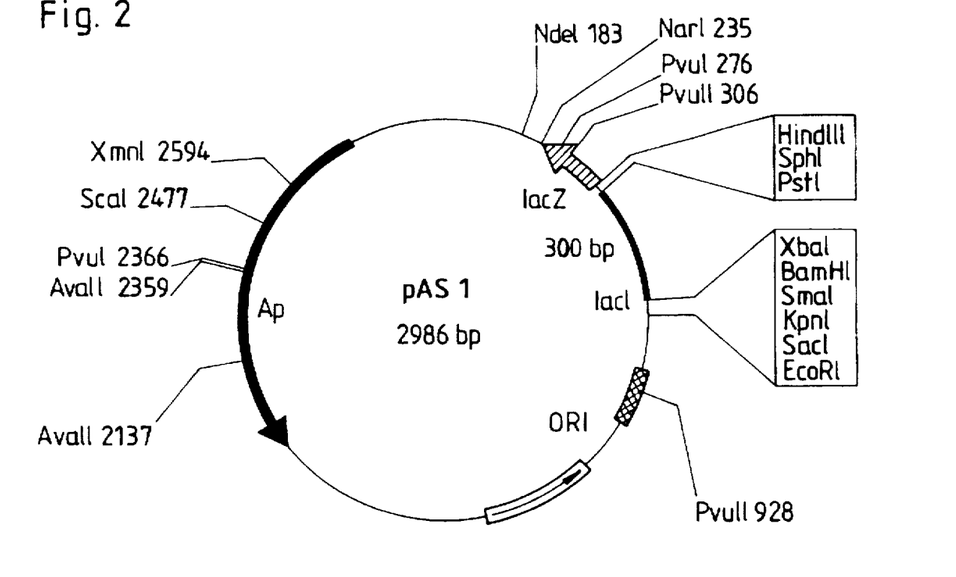
FIG. 2 is a map of plasmid pAS1.

The gene probe used for the screening was obtained from Actinoplanes sp. SE50/110 by means of a PCR (polymerase chain reaction) using oligonucleotide primers (see Table 1) which have been derived from highly conserved protein regions of known dTDP-glucose dehydratase enzymes. The amplified Actinoplanes sp. SE50/110 DNA fragment was cloned in pUC18 and transformed into E. coli DH5α (Gibco BRL, Eggenstein, Germany). The resulting plasmid (pAS1, see FIG. 2) was isolated from E. coli by the boiling method or by alkaline lysis (Sambrook et al., 1989).

The plasmid pAS1 from E. coli DH5α was hydrolyzed with the restriction enzymes EcoRI and HindIII. The 0.3 kb EcoRI/HindIII fragment was isolated and labelled by so-called Nick translation with $^{32}$P-labelled deoxynucleotides. This radiolabelled fragment was used as gene probe for isolating acarbose biosynthesis genes and is referred to hereinafter as acb probe.

Acarbose biosynthesis genes were isolated as follows. Chromosomal DNA from Actinoplanes sp. was cleaved with various restriction enzymes (SstI, BglII and BamHI), subjected to gel chromatography and investigated for homologous genes by Southern hybridization with the acb probe. DNA restriction fragments hybridizing with the gene probe have the following sizes: 10 kb (SstI), 9–10 kb (BglII) and 2.2 kb (BamHI). The various DNA fragments hybridizing with the acb probe were eluted from the gel, ligated into the vector pUC 18 and cloned in E. coli DH5α.

Figure 3:
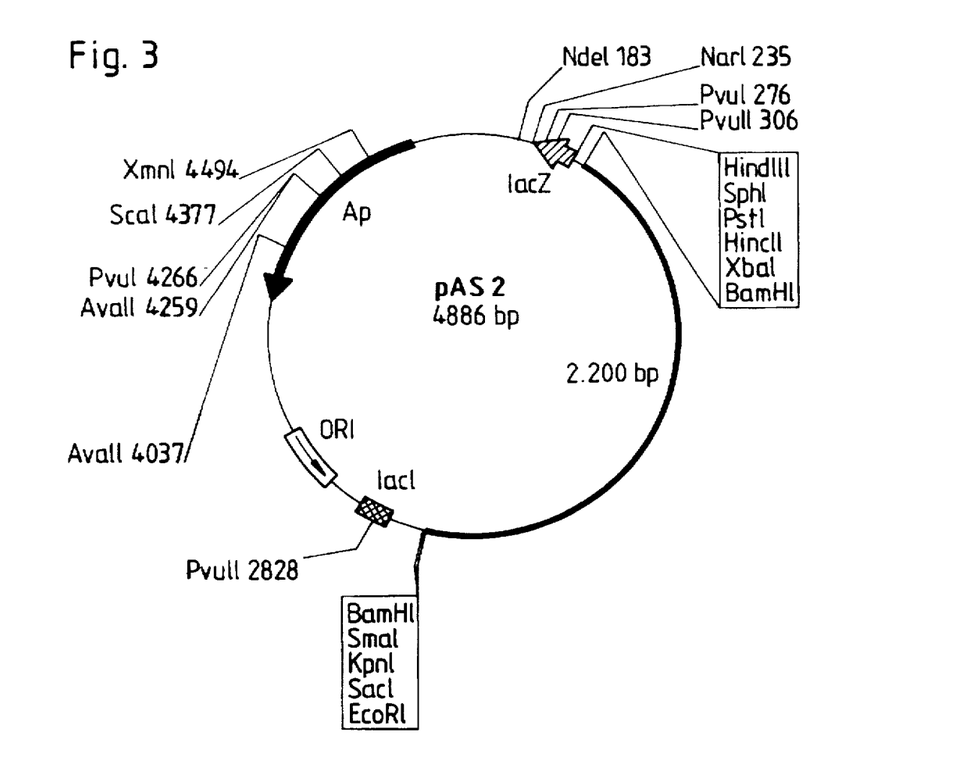
FIG. 3 is a map of plasmid pAS2.

The 2.2 kb BamHI DNA fragment was preferably cloned and sequenced. E. coli DH5α clones which contain Actinoplanes sp. DNA hybridizing with the acb probe were identified by pool hybridization (see Point 7). The plasmid DNA was isolated from the positive clones, and the result of the pool hybridization was verified by Southern hybridization. The resulting plasmid (see FIG. 3) was subjected to a cleavage with various restriction endonucleases, and the resulting DNA fragments were subcloned in pUC18 in E. coli DH5α, and religated and sequenced.

Figure 4:
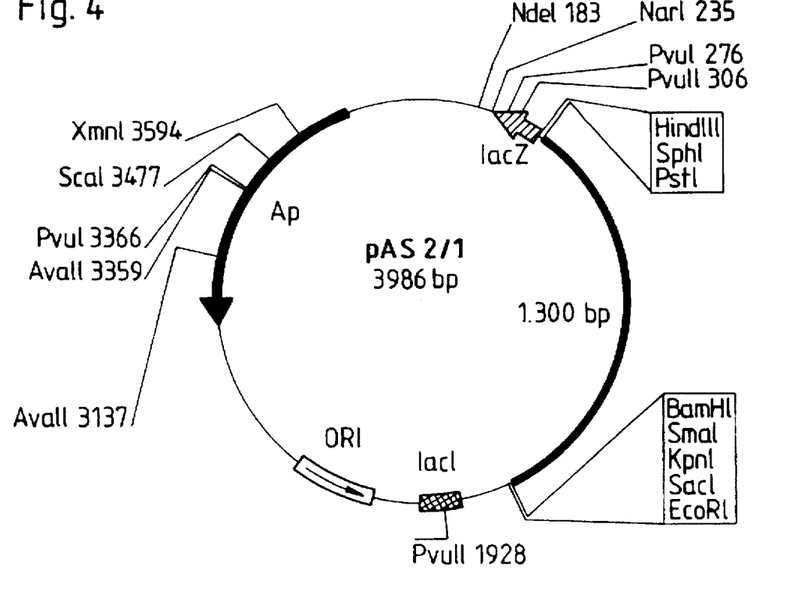
FIG. 4 is a map of plasmid pAS2/1.
Figure 5:
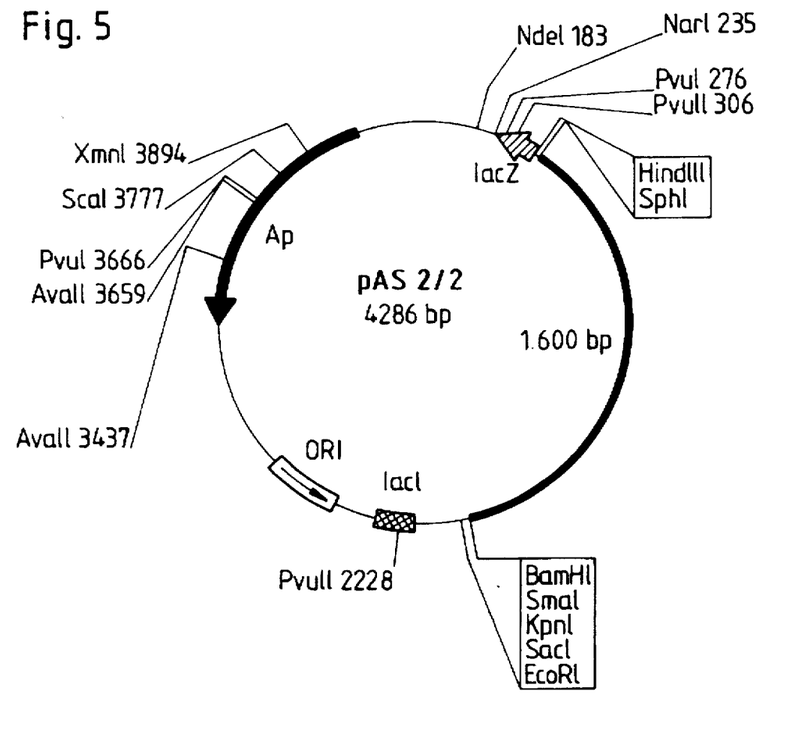
FIG. 5 is a map of plasmid pAS2/2.
Figure 6:
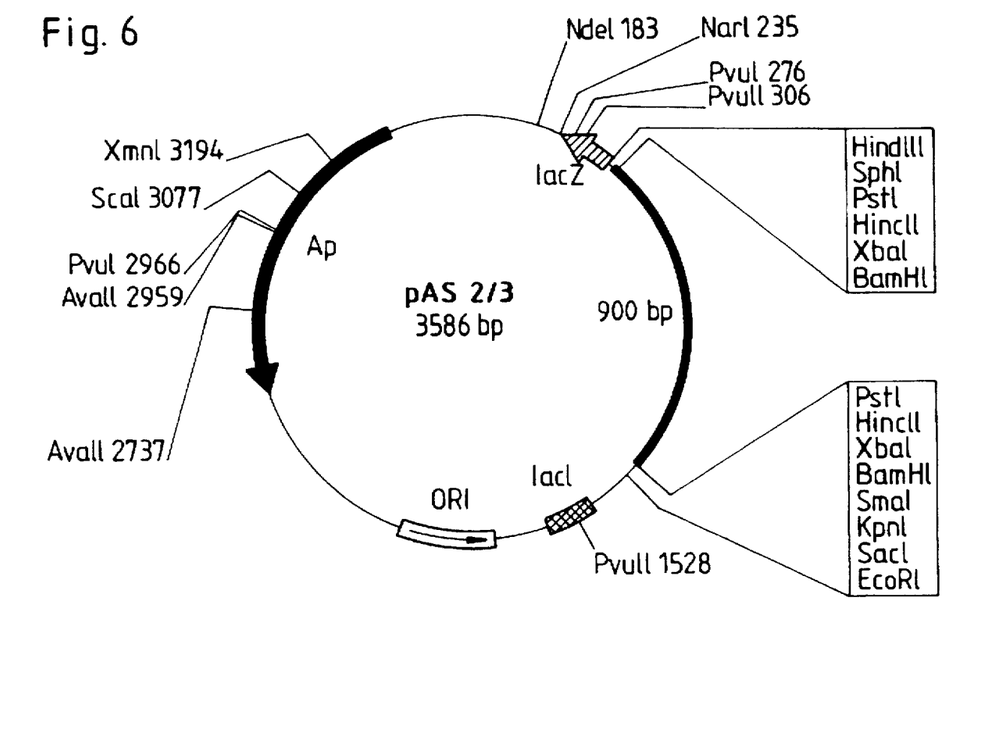
FIG. 6 is a map of plasmid pAS2/3.
Figure 7:
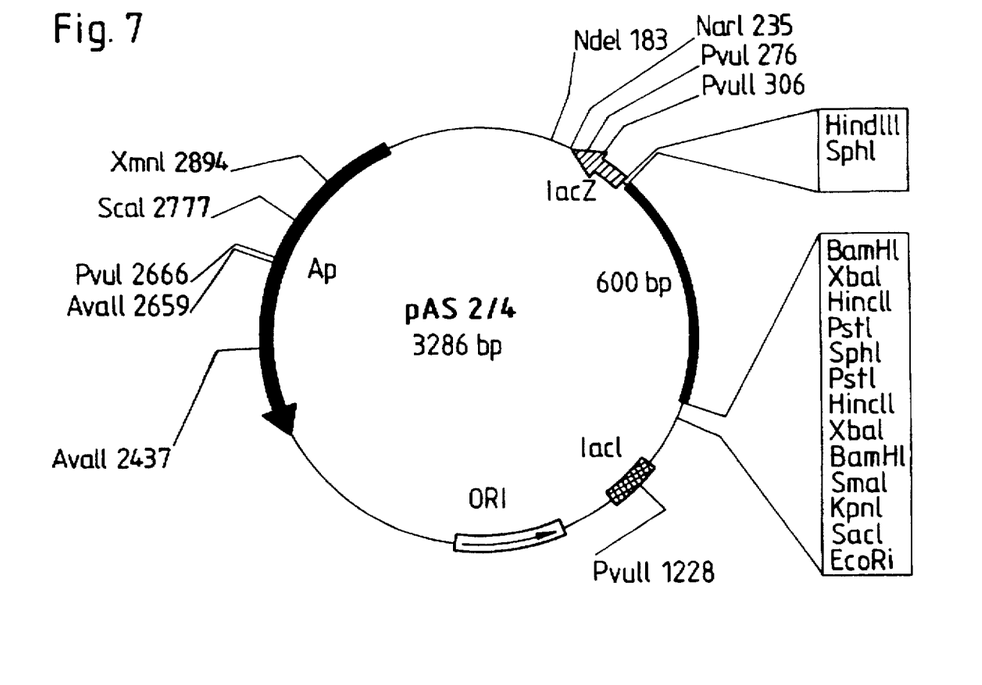
FIG. 7 is a map of plasmid pAS2/4.
Figure 8:
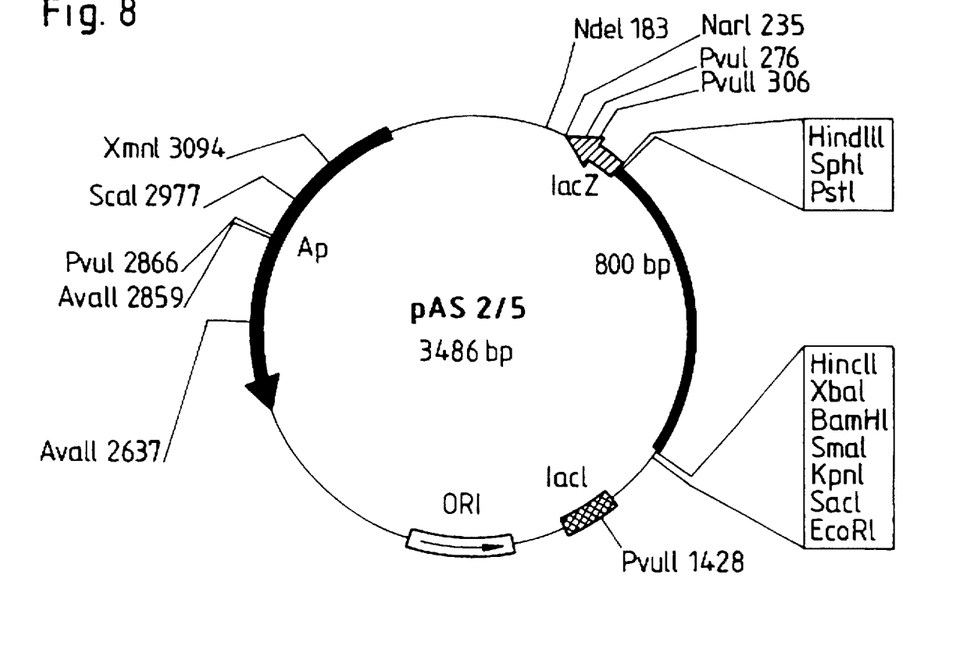
FIG. 8 is a map of plasmid pAS2/5.
Figure 9:
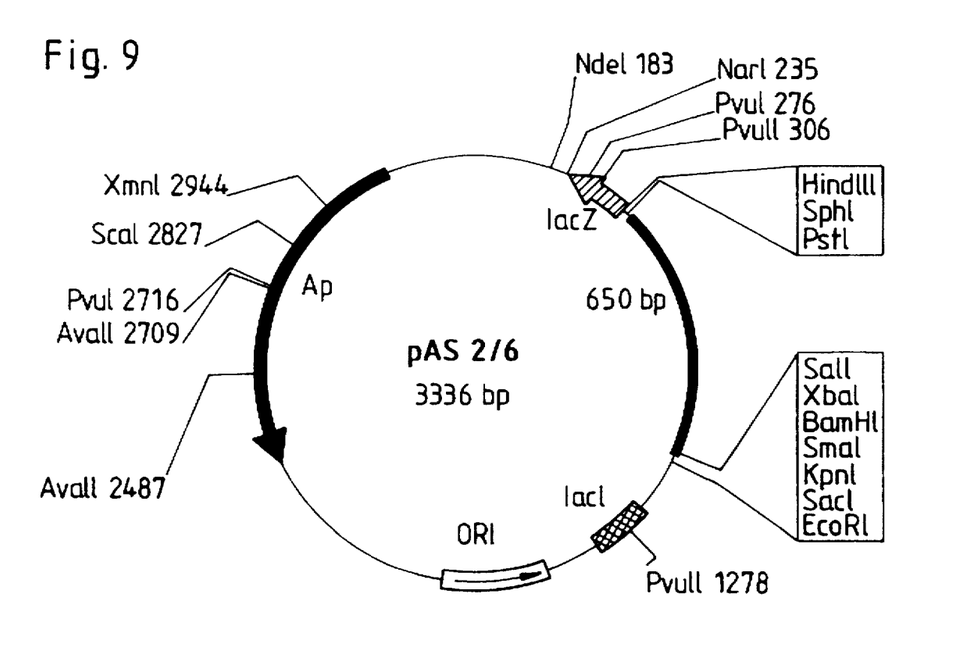
FIG. 9 is a map of plasmid pAS2/6.
Figure 10:
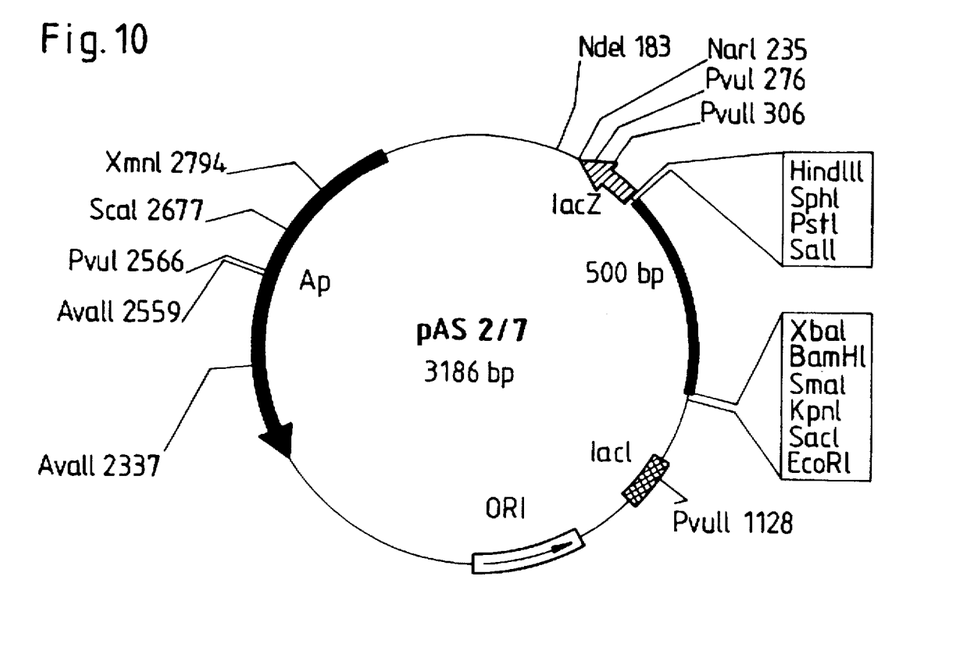
FIG. 10 is a map of plasmid pAS2/7.
Figure 11:
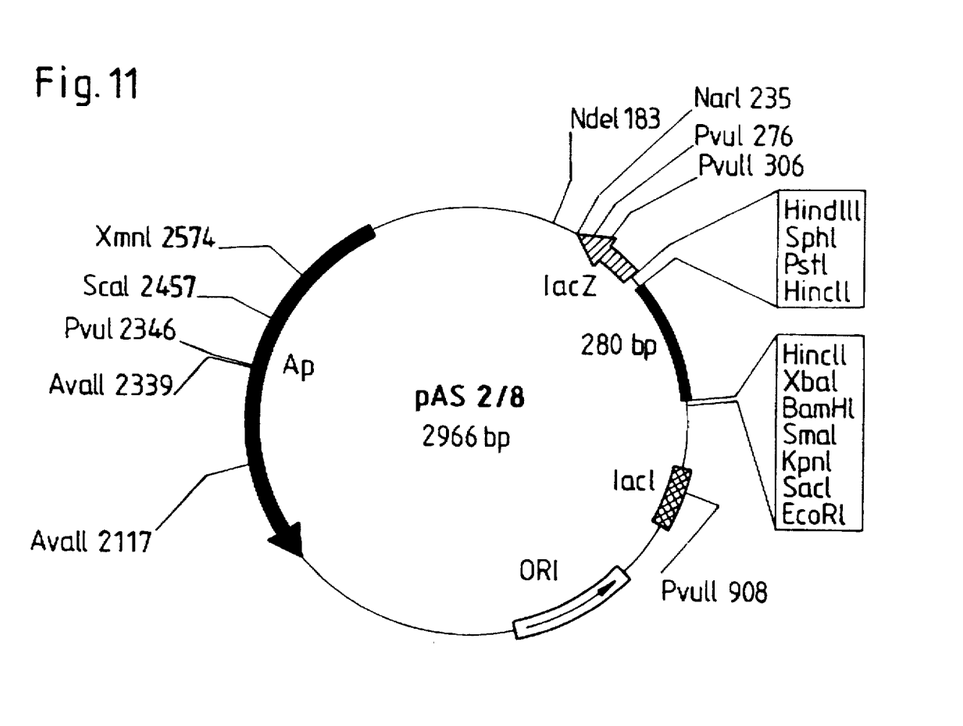
FIG. 11 is a map of plasmid pAS2/8.
Figure 12:
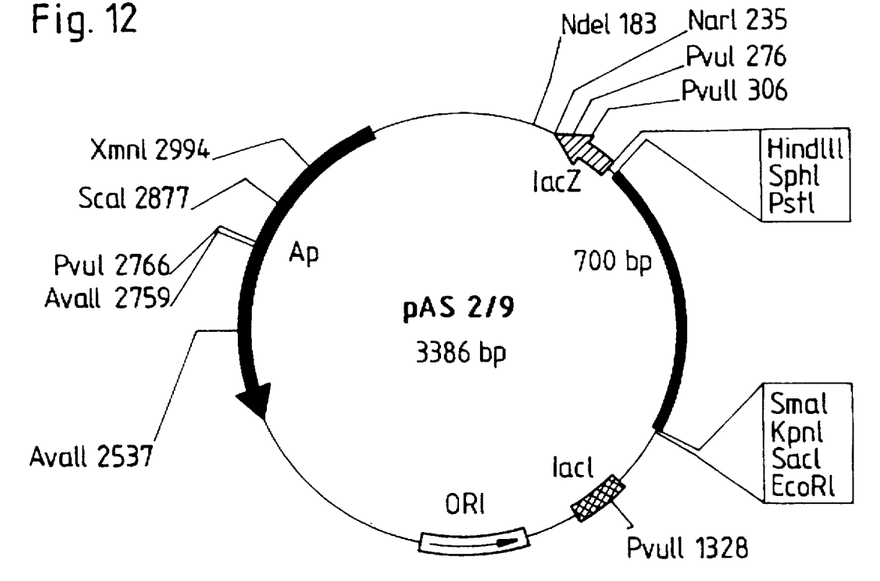
FIG. 12 is a map of plasmid pAS2/9.
Figure 13:
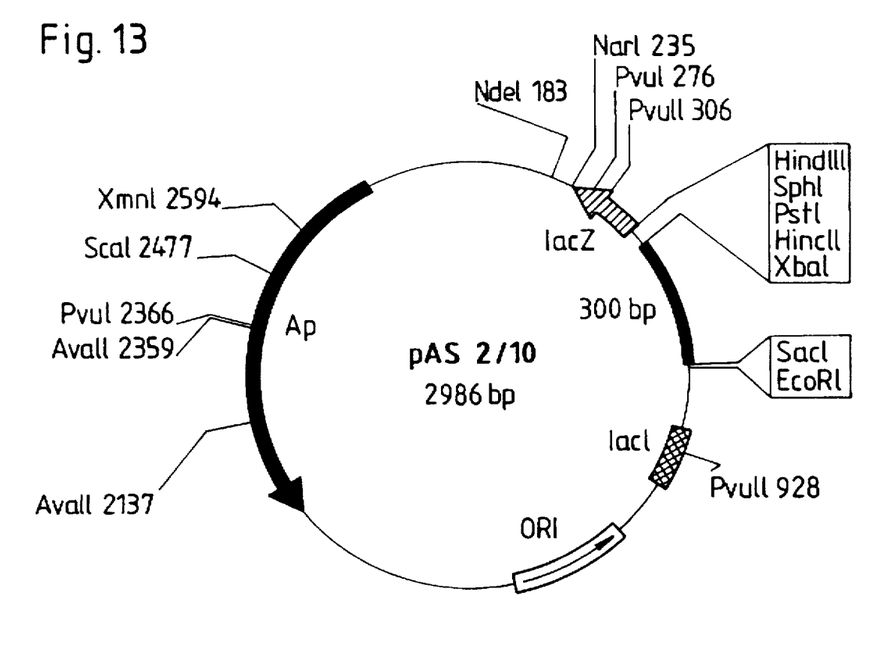
FIG. 13 is a map of plasmid pAS2/10.

To determine the DNA sequence of the 2.2 kb BamHI fragment of Actinoplanes sp., the following plasmids were constructed (see Point 7), and the sequence of the insert DNA was analyzed: (see FIGS. 1, 14)

pAS 2/1=1.3 kb PstI/BamHI fragment from pAS2 (FIG. 4)

pAS 2/2=1.6 kb SphI/BamHI fragment from pAS2 (FIG. 5)

pAS 2/3=0.9 kb PstI fragment from pAS2 (FIG. 6)

pAS 2/4=0.6 kb SphI fragment from pAS2 (FIG. 7)

pAS 2/5=0.8 kb HincII/HindIII fragment from pAS2/1 (FIG. 8)

pAS 2/6=0.65 kb XhoI/SaiII fragment from pAS2 (FIG. 9)

pAS 2/7=0.5 kb XhoI/SaiII fragment from pAS2 (FIG. 10)

pAS 2/8=0.28 kb HincII fragment from pAS2/3 (FIG. 11)

pAS 2/9=0.7 kb XhoI/BclI fragment from pAS2/1 (FIG. 12)

pAS 2/10=0.3 kb SstI/BclI fragment from pAS2 (FIG. 13)

The method of F. Sanger et al. (1977) or a method derived therefrom was used for the DNA sequencing. The Autoread sequencing kit (Pharmacia, Freiburg, Germany) was employed in conjunction with the automated laser fluorescence (ALF) DNA sequencer (Pharmacia, Freiburg, Germany). Suitable fluorescein-labelled pUC reverse sequencing and sequencing primers were purchased (Pharmacia, Freiburg, Germany; see Table 1).

Primers for the PCR:

| Primer name | Sequence |
|---|---|
| AS 2 | 5' GCCGCCGAATCCCATGTGGAC 3' (SEQ ID NO: 2) |
| AS 5 | 5' CCCGTAGTTGTTGGAGCAGCGGGT 3' (SEQ ID NO: 3) |

Primers for the sequencing reaction:

| Primer name | Sequence |
|---|---|
| universal primer | 5' GTAAAACGACGGCCAGT 3' (SEQ ID. NO: 4) |
| reverse primer | 5' GAAACAGCTATGACCATG 3' |

EXAMPLES

Example 1

Cultivation of the E. coli strains, preparation of the plasmid DNA and isolation E. coli DH5α was incubated in LB medium at 37° C. Plasmid-harbouring bacteria were maintained under selection pressure (ampicillin, 100 µg/ml). Cultivation took place on an orbital shaker at 270 rpm. Mixtures incubated for at least 16 h were designated overnight cultures (OC).

The cells from 1.5 ml of an OC incubated under selection pressure were used for preparation of plasmid DNA. The plasmids were isolated by the alkaline SDS lysis method (Birnboim & Doly 1979).

For specific hydrolysis of vector DNA, exclusively restriction endonucleases were used in accordance with the manufacturer's instructions (Gibco BRL, Eggenstein, Germany). 5 U of the particular restriction endonuclease were used to restrict 10 µg of plasmid DNA, incubating at 37° C. for 2 h. In order to ensure complete hydrolysis, the same amount of restriction endonuclease was added a second time and renewed incubation was carried out for at least 1 h.

The cleaved DNA was subjected to electrophoresis on 0.5–1.2% horizontal agarose gels, depending on the size of the DNA fragments. For the elution, the piece of gel which contained the DNA fragment was cut out with a sterile scalpel and weighed. The DNA fragments were eluted from the agarose using the JETsorb kit as instructed (Genomed, Bad Oeynhausen, Germany).

Example 2

Cultivation of Actinoplanes sp. preparation, cleavage of the chromosomal DNA and gel electrophoresis Actinoplanes sp. SE50/110 was incubated in TSB medium on an orbital shaker at 30° C. for 3 d. The preculture (5 ml) took place in culture tubes at 240 rpm, and the main culture (50 ml) took place in 500 ml flasks with baffles at 100 rpm. After the cultivation, the cells were sedimented by centrifugation and washed twice in TE buffer.

The complete DNA was prepared using 1.5–2 mg of cells (fresh weight) by the phenol/chloroform extraction method (D. A. Hopwood et al. 1985).

Hydrolysis of 20 µg of chromosomal DNA was carried out with 10 U of the appropriate restriction enzyme (Gibco BRL, Eggenstein, Germany) in the relevant buffer at 37° C. for 2 h. In order to ensure complete hydrolysis, the same amount of restriction endonuclease was added a second time, and renewed incubation was carried out for at least 1 h.

The cleaved DNA was subjected to electrophoresis on 0.7% horizontal agarose gels.

DNA fragments were once again eluted using the JETsorb kit (see Point 1).

Example 3

Preparation of the acb gene probe

The fragment from pAS1 prepared as in Point 1 was radiolabelled using the Nick translation system manufactured by Gibco BRL, Eggenstein, Germany, as stated by him. 0.5–1.0 µg of DNA fragment was used for this. [$\alpha$-$^{32}$P] dCTP was used (3000 Ci/mmol; Amersham, Braunschweig, Germany). The mixture was then boiled for 10 minutes (denaturation) and immediately added to the hybridization solution (see Point 4).

Example 4

DNA transfer to membranes, DNA hybridization (Southern hybridization) and autoradiography DNA fragments were transferred from agarose gels to membranes by the Southern transfer method (Southern, E. M., 1975). The agarose gels obtained as in Point 2 were shaken in 0.25M HCl for 20 minutes. The gels were placed on 3 layers of absorbent Whatman 3MM paper (Whatman, Maidstone, England), and a Hybond™-N+membrane (Amersham, Braunschweig, Germany) was placed on top free of air bubbles. Several layers of absorbent paper were placed on top of this. A weight weighing about 1 kg was placed on the stack of filters. The DNA is transferred by sucking through 0.4 m NaOH. After a transfer time of at least 12 h, the nylon filters were rinsed with 2×SSC for 5 minutes and dried in air.

The nylon filters were then shaken in 50–100 ml of prehybridization solution in a water bath at 68° C. for at least 2 h. The solution was changed at least twice during this. The hybridization took place in the hybridization cabinet for at least 12 h. 15 ml of hybridization solution which contained the acb probe (see Point 3) were used.

The nylon filters were then washed with 6× postwash and 1× postwash for 15 minutes each time. The nylon filters were then covered while still in the moist state with cling film.

Autoradiography takes place with Hyperfilm MP (Amersham, Braunschweig, Germany) in a lightproof cassette with intensifying screen at −80° C. for at least 16 h.

Example 5

Isolation and cloning of BamHI fragments from the complete DNA of Actinoplanes sp.

Chromosomal DNA from Actinoplanes sp. SE50/110 was completely hydrolyzed with BamHI and subjected to agarose gel electrophoresis, and the DNA fragments of length 1.5–3 kb were eluted from the agarose. The vector plasmid pUC18 was prepared from E. coli DH5α, hydrolyzed with BamHI and treated with alkaline phosphatase (Boehringer, Mannheim, Germany) in accordance with the manufacturer's instructions. Ligation took place in a volume of 20 µl, with the ratio of fragment to vector being 3:1, using 0.01–0.1 µg of DNA in the mixture. 1 U of T4 DNA ligase was used with the appropriate buffer (Gibco BRL, Eggenstein, Germany). Transformation-competent cells of E. coli DH5α were transformed with complete ligation mixtures (as described by Hanahan 1983). Ampicillin-resistant transformants were transferred to LB-Amp selection plates (100 µg/ml).

Example 6

Identification of clones which contain the dTDP-D-glucose synthase gene

Ampicillin-resistant transformants were investigated for the presence of the dTDP-D-glucose synthase gene. In each case, ten of these clones were streaked onto a selection plate, incubated overnight and washed off the plate with 3 ml of LB medium. The plasmid DNA was then isolated from 20 of such pools of ten (as described by Birnboim & Doly, 1979). In order to delete the cloned BamHI fragments from the polylinker, the 20 different plasmid preparations were hydrolyzed with the restriction endonucleases EcoRI and HindIII. The restriction mixtures were then subjected to electrophoresis on a 0.8% agarose gel, and the DNA was transferred by Southern transfer from the agarose gel to a nylon filter (see Point 4). Hybridization took place once again with the acb probe (see Point 4). One of the pools reacted positively with the acb probe and was fractionated into the ten individual clones. The plasmids thereof were likewise isolated and subjected to the procedure described above. The hybridizing plasmid was called pAS2. It contains a 2.2 kb BamHI fragment.

Example 7

Subcloning of the plasmid pAS2

Figure 1:
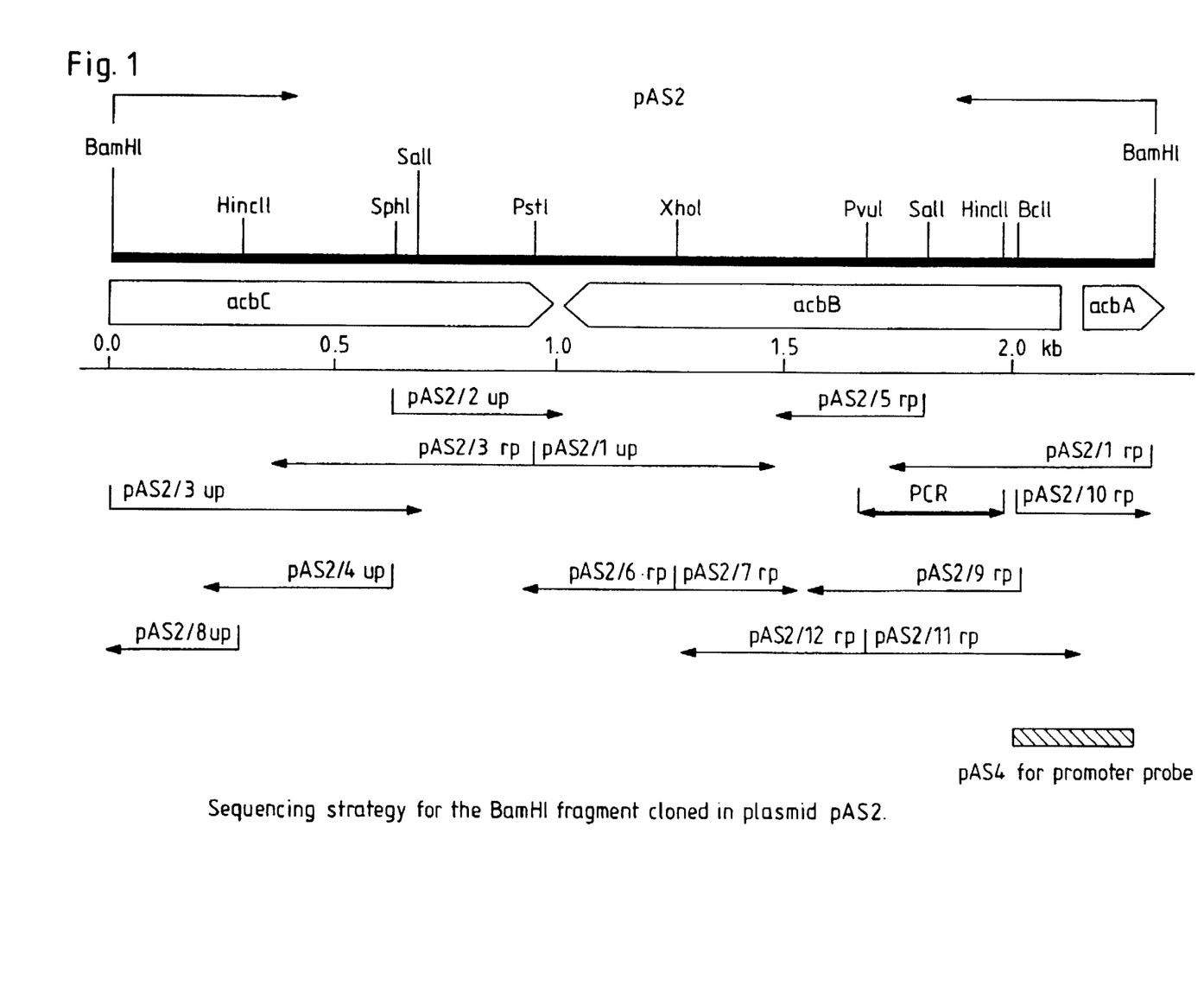
FIG. 1 is a schematic showing the sequencing strategy for the BamHI fragment cloned in plasmid pAS2.

Starting from the plasmid pAS2, several subclones were produced in order to elucidate the sequence of the double-stranded DNA (FIG. 1; FIGS. 4–13).

pAS2/1 and pAS2/3)

The plasmid pAS2 was hydrolyzed with PstI. The restriction mixture was separated on a 1% agarose gel. The 0.9 kb PstI fragment resulting from the hydrolysis and the plasmid band with the remaining 1.3 kb PstI/BamHI fragment were eluted from the agarose gel (JETsorb kit; Genomed, Bad Oeynhausen, Germany). The plasmid with the 1.3 kb PstI/BamHI fragment was religated to give subclone pAS2/1. The 0.9 kb PstI fragment was cloned in the vector pUC18 (hydrolyzed with PstI) to result in the subclone pAS2/3.

pAS2/2 and pAS2/4)

The plasmid pAS2 was hydrolyzed with SphI. The plasmid with the 1.6 kb SphI/BamHI fragment was religated to give the subclone pAS2/2. The 0.6 kb SphI fragment was cloned in pUC18 (hydrolyzed with SphI) to result in the subclone pAS2/4.

pAS2/5)

The plasmid pAS2/1 was hydrolyzed with HincII/HindIII. The resulting 0.8 kb fragment was cloned in pUC18 (hydrolyzed with HindIII/HincII) to result in subclone pAS2/5.

pAS2/6)

The plasmid pAS2 was hydrolyzed with XhoI/SalI. The resulting 0.65 kb fragment was cloned in pUC18 (hydrolyzed with SalI) to result in subclone pAS2/6.

pAS2/7)

The plasmid pAS2 was hydrolyzed with XhoI/SalI. The resulting 0.5 kb fragment was cloned in pUC18 (hydrolyzed with SalI) to result in subclone pAS2/7.

pAS2/8)

The plasmid pAS2/3 was hydrolyzed with HincII. The resulting 0.3 kb fragment was cloned in pUC18 (hydrolyzed with HincII) to result in subclone pAS2/8.

pAS2/9)

The plasmid pAS2/1 was hydrolyzed with XhoII/BclI. The resulting 0.7 kb fragment was cloned in pUC18 (hydrolyzed with SalI/BamHI) to result in subclone pAS2/9.

pAS2/10)

The plasmid pAS2 was hydrolyzed with SstI/BclI. The resulting 0.3 kb fragment was cloned in pUC18 (hydrolyzed with SstI/BamHI) to result in subclone pAS2/10.

Example 8

DNA sequencing of the 2.2 kb BamHI fragment of Actinoplanes sp.

The plasmids described in Point 7 were sequenced. 6–8 µg of plasmid DNA from one preparation (see Point 1) were used in the sequencing reaction. The sequencing reaction was carried out using the Auto-Read sequencing kit (Pharmacia, Freiburg, Germany). The standard protocol for sequencing dsDNA was used in this case. In order to make it possible to analyze the nucleotide sequence using the A.L.F. (automated laser fluorescence (DNA) sequencer), the fluorescein-labelled universal and reverse sequence primers were used as starter molecules for the sequencing reaction (see Table 1). To prepare the gel, 8 ml of Hydro Link Long Ranger (Serva, Heidelberg, Germany), 33.6 g of urea, 8 ml of 10×TBE buffer, ad 80 ml with H$_2$O were mixed, sterilized by filtration and degassed for 1 minute. The polymerization was initiated by adding 350 µl of 10% (w/v) ammonium persulphate and 40 µl of N,N,N',N'-tetramethylethylenediamine. The solution was poured into a gel mould (50×50×0.05 cm). Electrophoresis took place at 38 W and a constant temperature of 45° C. 1× TBE buffer was used as running buffer. Conversion of the metered fluorescence to a DNA sequence took place in an on-line computer (Compaq 386/20e) which also served to control the electrophoresis unit (Program A.L.F. Manger 2.5; Pharmacia).

Buffers and solutions:

Media for cultivating bacteria

LB medium:

| | |
|---|---|
| Tryptone | 10 g |
| NaCl | 10 g |
| Yeast extract | 5 g |
| H$_2$O | ad 1000 ml |

The pH was adjusted to 7.5 with 4M NaOH.

TSB medium:

| | |
|---|---|
| Tryptone soya broth (Oxoid) | 30 g |
| H$_2$O | ad 1000 ml |

TE buffer (pH 8.0)

| | |
|---|---|
| Tris HCl | 10 mM |
| Na$_2$ EDTA | 1 mM |

Standard preparation of plasmid DNA
(modif. of Birnboim & Doly 1979 method)

| | |
|---|---|
| Mix I: | 50 mM glucose |
| | 50 mM tris HCl (pH 8.0) |
| | 10 mM EDTA (pH 8.0) |
| | 5 mg/ml lysozyme |
| Mix II: | 200 mM NaOH |
| | 1% (w/v) SDS (sodium dodecyl sulphate) |
| Mix III: | 3M potassium acetate |
| | 1.8M formate |

DNA-DNA hybridization

| | |
|---|---|
| 20 × SSC: | 3M NaCl |
| | 0.3M Na citrate |
| | pH 7.2 |

Prehybridization solution:

| | |
|---|---|
| 6 × SSC: | 0.01M sodium phosphate buffer pH 6.8 |
| | 1 mM EDTA |
| | 0.5% SDS |
| | 0.1% skimmed milk powder |

Hybridization solution:

The acb probe after the labelling reaction is added to 15 ml of prehybridization solution.

| | |
|---|---|
| 6 × postwash: | 6 × SSC |
| | 0.5% SDS |

DNA sequencing:

| | |
|---|---|
| TBE buffer (pH 8.0): | 1M tris base |
| | 0.83M boric acid |
| | 10 mM EDTA |

References

1. Birnboim H. C. & Doly J. (1979)
   A rapid alkaline extraction procedure for screening recombinant plasmid DNA Nucleic Acids Res.; 7, 1513–1523
2. Hanahan D. (1983)
   Studies on transformation of Escherichia coli with plasmids J. Mol. Biol.: 166, 557–580
3. Hopwood D. A. et al., (1985)
   Genetic manipulation of Streptomyces;
   A laboratory manual; The John Innes Foundation, Norwich, England 4. Sanger F.; Nicklen S.; Coulson A. R. (1977) DNA sequencing with chain-terminating inhibitors Proc. Natl. Acad. Sci. USA, 74, 5463–5467
5. Southern E. M., (1975) Detection of specific sequences among DNA Fragments separated by gel electrophoresis J. Mol. Biol., 98, 503–521

We claim:

1. An isolated and purified DNA fragment selected from the group consisting of:

(A) a DNA fragment comprising a nucleotide sequence encoding the amino acid sequence of acbB of SEQ ID NO: 1;

(B) a DNA fragment comprising a nucleotide sequence encoding the amino acid sequence of acbA of SEQ ID NO: 1; and (C) a DNA fragment comprising a nucleotide sequence encoding the amino acid sequence of acbC of SEQ ID NO: 1.

2. A vector comprising a DNA fragment according to claim 1.

* * * * *